United States Patent [19]
Rossignol

[11] Patent Number: 5,859,038
[45] Date of Patent: *Jan. 12, 1999

[54] METHOD FOR TREATMENT OF HELICOBACTER PYLORI INFECTIONS

[75] Inventor: Jean-François Rossignol, Clearwater, Fla.

[73] Assignee: Romark Laboratories, L.C., Tampa, Fla.

[ * ] Notice: The term of this patent shall not extend beyond the expiration date of Pat. No. 5,578,621.

[21] Appl. No.: 644,153

[22] Filed: May 10, 1996

Related U.S. Application Data

[63] Continuation-in-part of Ser. No. 301,407, Sep. 8, 1994, Pat. No. 5,578,621.

[51] Int. Cl.⁶ .................................................. A61K 31/425
[52] U.S. Cl. .............................................................. 514/371
[58] Field of Search ............................................. 514/371

[56] References Cited

U.S. PATENT DOCUMENTS 3,950,351   4/1976   Rossignol ................................ 548/192

*Primary Examiner*—Robert Gerstl
*Attorney, Agent, or Firm*—Pendorf & Cutliff

[57] ABSTRACT

The present invention relates to a method for treating helicobacter pylori bacteria or for preventing troubles or diseases or infections due to helicobacter pylori bacteria, said method comprising administering to a subject an effective amount of a compound selected in the group consisting of:

compound A of formula

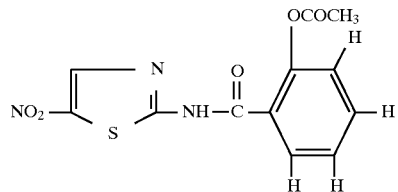

compound B of formula

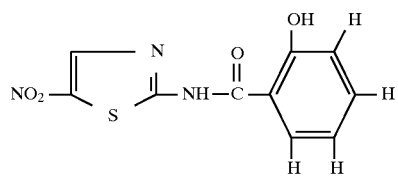

and mixture of said compounds A and B.

18 Claims, No Drawings

METHOD FOR TREATMENT OF HELICOBACTER PYLORI INFECTIONS

This application is a continuation-in-part of application Ser. No. 08/301,407 filed Sep. 8, 1994 now U.S. Pat. No. 5,578,621.

THE PRIOR ART

Nitrothiazole compound PH 5776 (2-(acetolyloxy)-N-(5-nitro 2-thiazolyl) benzamide) is a compound A of formula:

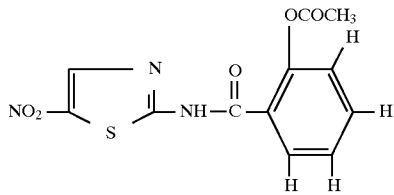

The preparation and uses of this compound are disclosed in U.S. Pat. No. 3,950,351, as well as in publication made by applicant.

Compound B is a compound of formula:

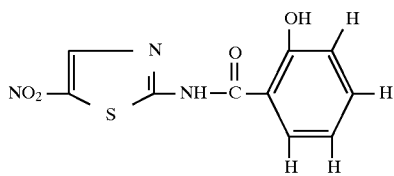

The preparation and uses of this compound is disclosed in U.S. Pat. No. 08/301,407 patent application, U.S. Pat. No. 08/383,855 and WO 95/28393, the content of which is incorporated herewith by reference.

Helicobacter pylori is a major etiologic factor in peptic ulcer diseases and has an important role in gastric cancer. Up to now, the only satisfactory treatment for obtaining an eradication of Helicobacter pylori at a satisfactory rate consists in the administration of at least two different antibiotics and of an antisecretory agent or agent for increasing the pH.

Antibiotics which are currently use for treating helicobacter pylori are metronidazole, ciprofloxacin and amoxicillin. The major problem occurring with known antibiotics such as metronidazole is the formation of a cross resistance, whereby strains of helicobacter pylori will no more be satisfactory treated by said antibiotics.

The present invention has for subject matter compounds which can be used alone for treating on a satisfactory level helicobacter pylori with a low minimum inhibition concentration.

BRIEF DESCRIPTION OF THE INVENTION

The invention relates to a method for treating helicobacter pylori bacteria or for preventing infections, troubles or diseases caused by helicobacter pylori bacteria or for preventing gastric cancer, comprising administering to a subject, for example a subject in need of treatment, an effective amount of a compound selected in the group consisting of:

compound A of formula

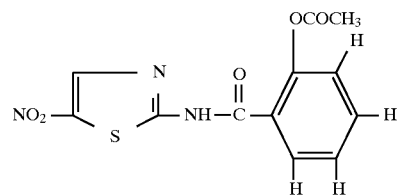

compound B of formula

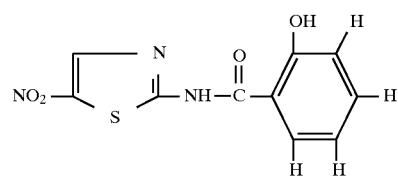

and mixtures of said compounds A and B.

While compound A as such can satisfactory be used in the method of the invention, mixtures of compounds A and B are also suitable for the method. The weight content of compound A with respect to the weight of compounds A and B can vary from 0 to 100%, for example from 99 to 100% (i.e. substantially pure compound A), or from 80 to 99% (mixtures known for their antiviral activity—see USSN ), or from 0 to 80%. In the latter case the weight content is preferably from 25 and 75%.

According to an embodiment of the method of the invention, the method comprises the step of administering, prior the administration of compound A and/or compound B or after the administration of compound A and/or compound B or during the administration of compound A and/or compound B, another antibacterial agent, preferably a compound selected in the group consisting of metronidazole, ciproflaxin, amoxicillin, amoxicillin-clavulanic acid, piperacillin, cefoxitin, imipenem and clindamycin.

Description of Tests

The strains which were tested are 31 strains of Helicobacter pylori. Said strains were isolated from patients suffering symptomatic and histologically confirmed gastritis. The strains were maintained frozen at −70° C.

The bacteriostatic activity of compounds of the invention and of metronidazole was evaluated using the measurement of the minimum inhibition concentration (MIC) of the strains.

The MICs were determined using the agar dilution method according to the following procedure:
  Culture medium
    Mueller Hinton 2 agar (BioMerieux—France)
    10% sheep blood (Eurobio)
    polyvitex
  Bacterial inoculation
    A suspension of approximately 109 CFU/ml was prepared in brucella broth medium using a 48 hour agar culture at 37° C.
  Preparation of antibiotic dilutions and agar plates
    A 2,000 mg/l solution of each antibiotic was prepared as follows:
    nitazoxanide and tizoxanide in DMSO
    metronidazole in water
    Dilutions were subsequently prepared from 128 mg/ml up to 0.25 mg/ml. Each plate contained:32 ml of agar, 4 ml of sheep blood, and 4 ml of the antibiotic solution, which was poured into 12 cm Petri plates.

Bacterial plating
A multiple tip inoculator derived from a Steers' apparatus was used.

Incubation
Incubation was performed in a microaerobic atmosphere during 48 hours to 72 hours at 37° C.

Reading
The MIC value was considered to be the lowest concentration inhibiting growth of the strain. It was recorded in mg/l.

The following table gives for each dilution of compounds tested: the number of strains killed, the percentage of strains killed (number/31×100).

| dilution (mg/ml) | 0.25 | 0.5 | 1 | 2 | 4 | 8 | more than 32 |
|---|---|---|---|---|---|---|---|
| Compound A | 2 (5%) | 8 (24%) | 21 (69%) | 28 (89%) | 30 (97%) | 31 (100%) | |
| Compound B | 4 (10%) | 8 (24%) | 23 (74%) | 29 (95%) | 30 (97%) | 31 (100%) | |
| Metronidazole | 0 | 2 (5%) | 12 (37%) | 16 (53%) | 21 (69%) | 23 (74%) | 31 (100%) |

The range of activity of compounds A and B on helicobacter pylori was from 0.25 to 8 mg/ml, while said range was from 0.5 to 128 mg/ml for metronizadole.

It has also been observed that mixtures of compounds A and B were efficient against helicobacter pylori.

Possible mixtures are: a mixture of compound A and compound B, the weight content of compound A with respect to the weight of said compounds A and B is greater than 99%;

a mixture of compound A and compound B, the weight content of compound A with respect to the weight of said compounds A and B is less than 80%;

a mixture of compound A and compound B, the weight content of compound A with respect to the weight of said compounds A and B is from 25% to 75% (for example about 50%).

The method of the invention (treatment or method for preventing infections or diseases, such as gastric cancer) comprises the step of administering an efficient amount of compound A and/or of compound B. When compounds A and B are used, compound A can be administered prior the administration of compound B, after the administration of compound B or during the administration of compound B. According to a specific method of the invention, a compound selected in the group consisting of metronidazole, ciproflaxin, amoxicillin, amoxicillin-clavulanic acid, piperacillin, cefoxitin, imipenem and clindamycin is administered prior the administration of compound A and/or 3, after the administration of compound A and/or B or during the administration of compound A and/or B.

Additional in vitro testing against 241 strains of obligate or facultative anaerobic gram positive and gram negative bacteria has shown that compounds A and B and their combinations were highly effective against these organisms.

The method disclosed hereabove can thus be used for the treatment of or for preventing troubles, diseases or infections caused by oligate and/or facultative gram positive and gram negative bacteria.

What I claim is:

1. A method for treating helicobacter pylori bacteria comprising administering to a subject in need of treatment an effective amount of a compound selected from the group consisting of:

compound A of formula

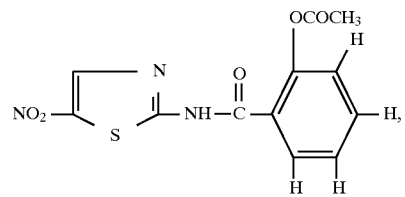

compound B of formula

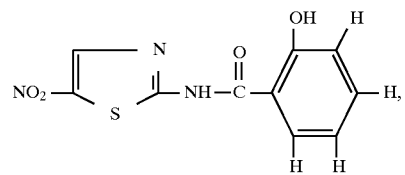

and a mixture of said compounds A and B.

2. The method of claim 1 comprising administering to a subject in need of treatment an effective amount of the compound A.

3. The method of claim 1 comprising administering to a subject in need of treatment an effective amount of the compound B.

4. The method of claim 1 comprising administering to a subject in need of treatment an effective amount of a mixture of compound A and compound B.

5. The method of claim 1 comprising administering to a subject in need of treatment an effective amount of a mixture of compound A and compound B, wherein the weight content of compound A with respect to the weight of said compounds A and B is greater than 99%.

6. The method of claim 1 comprising administering to a subject in need of treatment an effective amount of a mixture of compound A and compound B, wherein the weight content of compound A with respect to the weight of said compounds A and B is less than 80%.

7. The method of claim 1 comprising administering to a subject in need of treatment an effective amount of a mixture of compound A and compound B, wherein the weight content of compound A with respect to the weight of said compounds A and B is from 25% to 75%.

8. The method of claim 1, comprising administering to a subject in need of treatment an effective amount of a compound selected from the group consisting of:

compound A of formula

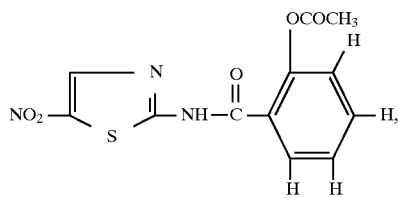

compound B of formula

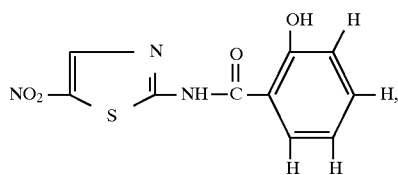

and a mixture of said compounds A and B, prior to administering to the subject a compound selected from the group consisting of metronidazole, ciproflaxin, amoxicillin, amoxicillin-clavulanic acid, piperacillin, cefoxitin, imipenem and clindamycin.

9. The method of claim 1, comprising administering to a subject in need of treatment an effective amount of a compound selected from the group consisting of:

compound A of formula

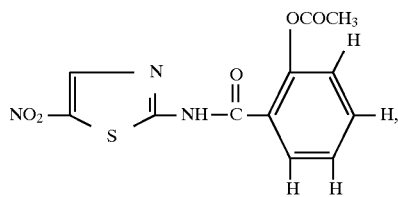

compound B of formula

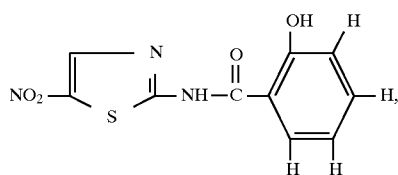

and a mixture of said compounds A and B, after administering to the subject a compound selected from the group consisting of metronidazole, ciproflaxin, amoxicillin, amoxicillin-clavulanic acid, piperacillin, cefoxitin, imipenem and clindamycin.

10. The method of claim 1, comprising administering to a subject in need of treatment an effective amount of a compound selected from the group consisting of compound A of formula

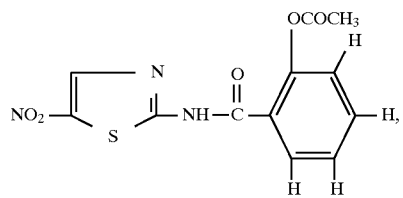

compound B of formula

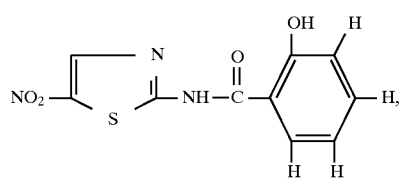

and a mixture of said compounds A and B, together with a compound selected from the group consisting of metronidazole, ciproflaxin, amoxicillin, amoxicillin-clavulanic acid, piperacillin, cefoxitin, imipenem and clindamycin.

11. A method for preventing infections caused by helicobacter pylori bacteria comprising administering to a subject an effective amount of a compound selected from the group consisting of:

compound A of formula

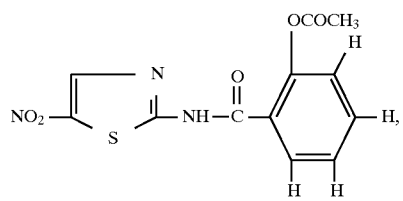

compound B of formula

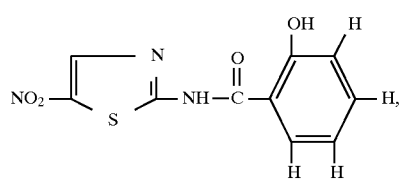

and a mixture of said compounds A and B.

12. The method of claim 11 comprising administering to a subject an effective amount of the compound A.

13. The method of claim 11 comprising administering to a subject an effective amount of the compound B.

14. The method of claim 11 comprising administering to a subject an effective amount of a mixture of compound A and compound B.

15. The method of claim 11 comprising administering to a subject an effective amount of a mixture of compound A and compound B, wherein the weight content of compound A with respect to the weight of said compounds A and B is greater than 99%.

16. The method of claim 11 comprising administering to a subject an effective amount of a mixture of compound A and compound B, wherein the weight content of compound A with respect to the weight of said compounds A and B is less than 80%.

17. The method of claim 11 comprising administering to a subject an effective amount of a mixture of compound A and compound B, wherein the weight content of compound A with respect to the weight of said compounds A and B is from 25% to 75%.

18. The method of claim 11, comprising administering to a subject an effective amount of a compound selected from the group consisting of:

compound A of formula

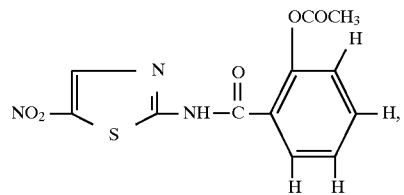

compound B of formula

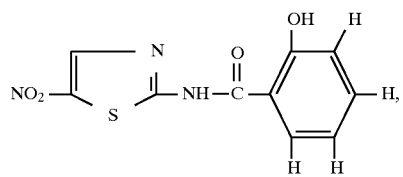

and a mixture of said compounds A and B, and an amount of a compound selected from the group consisting of metronidazole, ciproflaxin, amoxicillin, amoxicillin-clavulanic acid, piperacillin, cefoxitin, imipenem and clindamycin.

* * * * *